United States Patent [19]

Linger et al.

[11] Patent Number: 4,477,926
[45] Date of Patent: * Oct. 16, 1984

[54] PROCESS FOR INSPECTING AND AUTOMATICALLY SORTING OBJECTS SHOWING PATTERNS WITH CONSTANT DIMENSIONAL TOLERANCES AND APPARATUS FOR CARRYING OUT SAID PROCESS

[75] Inventors: Claude J. A. Linger, Paris; Gisele C. Locicero, Evry, both of France

[73] Assignee: International Business Machines Corporation, Armonk, N.Y.

[*] Notice: The portion of the term of this patent subsequent to Nov. 6, 2001 has been disclaimed.

[21] Appl. No.: 330,411

[22] Filed: Dec. 14, 1981

[30] Foreign Application Priority Data

Dec. 18, 1980 [EP] European Pat. Off. ......... 80430033.3

[51] Int. Cl.$^3$ .............................................. G06K 9/36
[52] U.S. Cl. ............................................ 382/8; 382/49
[58] Field of Search ................... 358/106; 364/489, 49; 250/562, 563; 382/8, 45, 51, 49

[56] References Cited

U.S. PATENT DOCUMENTS

| | | | |
|---|---|---|---|
| 3,645,626 | 2/1972 | Druschel | 356/71 |
| 3,868,508 | 2/1975 | Lloyd | 350/330 |
| 3,887,762 | 6/1975 | Uno et al. | 358/106 |
| 4,056,716 | 11/1977 | Baxter et al. | 358/106 |
| 4,269,515 | 5/1981 | Altman | 356/394 |
| 4,345,312 | 8/1982 | Yasuye et al. | 382/34 |

Primary Examiner—John C. Martin
Assistant Examiner—Erin A. McDowell
Attorney, Agent, or Firm—John J. Goodwin

[57] ABSTRACT

This invention relates to a process for inspecting and sorting objects showing patterns with constant dimensional tolerances as masks, integrated circuit chips, modules currently in use in the electronic industry. The process is based on the comparison of the image of a reference object $I_{ref}$ with the image of an object to be inspected $I_{exa}$. Images $I_{ref}$ and $I_{exa}$ after being picked up and sampled, are threshold to produce binary electronic images which are cleaned, then centered to allow the comparison of resulting electronic images $I_{REF}$ and $I_{EXA}$ to be carried out. The image processing includes the following operations: First of all constructing electronic images $I_{REF\,max}$ and $I_{REF\,min}$ respectively which are images $I_{REF}$ expanded and eroded by a structuring element adapted to the dimensional tolerances of the object to be inspected. Then, the images of the defects of the "spreading" type and of the "lack" type are constructed by respectively carrying out the following logic operations: $[I_{REF\,max} \text{ OR } I_{EXA}]$ EXC.OR $I_{REF\,max}$ and $[I_{REF\,min} \text{ OR } I_{EXA}]$ EXC.OR $I_{EXA}$. Then, the defect images are analyzed with respect to a predetermined reject criterion. At last, final sorting step is carried out. This invention also relates to an apparatus for carrying out said process. Said apparatus can comprise a digital computer for automatizing the various steps which are indicated above.

16 Claims, 15 Drawing Figures

A  B  C

A  B  C  D

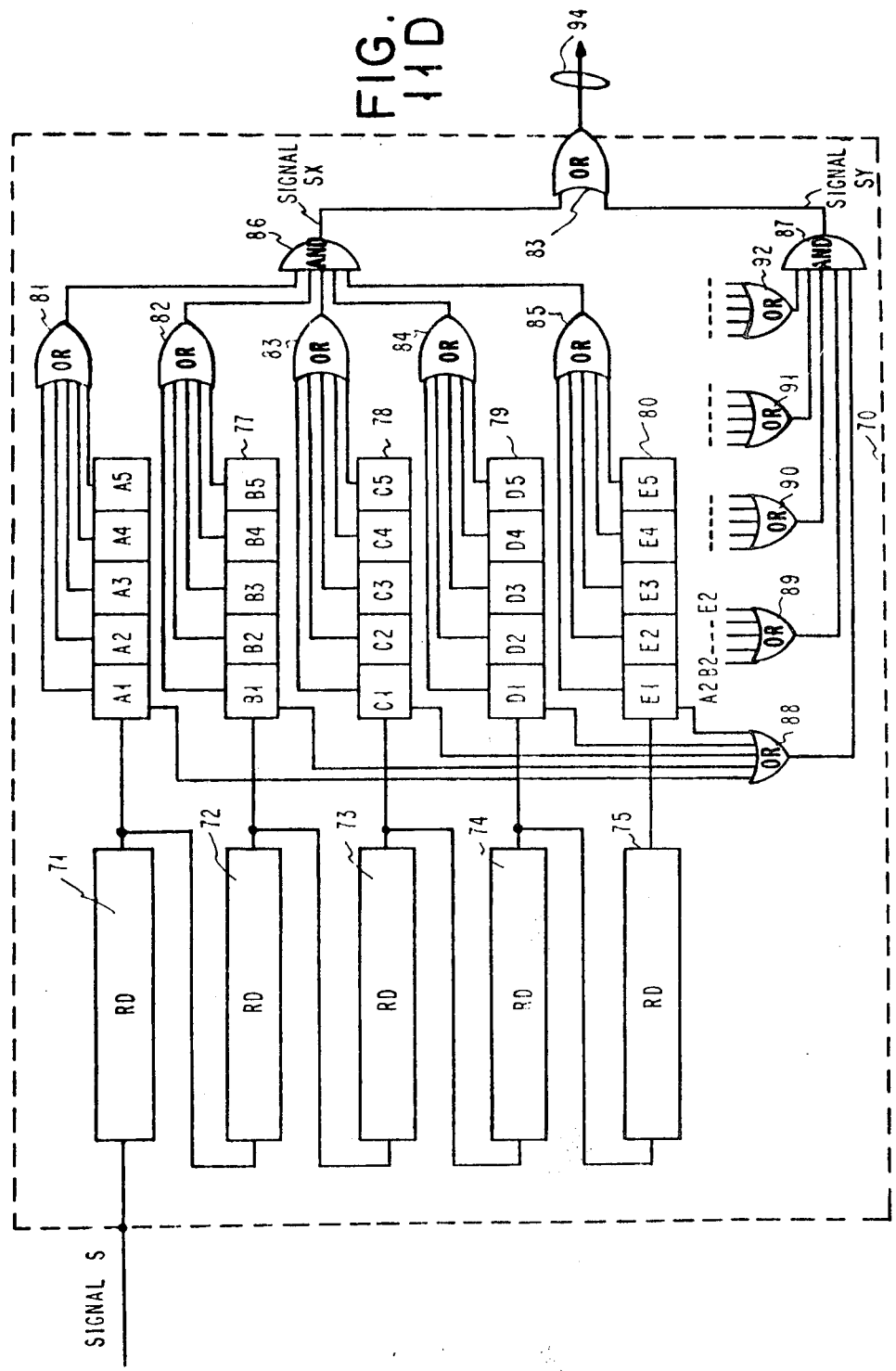

PROCESS FOR INSPECTING AND AUTOMATICALLY SORTING OBJECTS SHOWING PATTERNS WITH CONSTANT DIMENSIONAL TOLERANCES AND APPARATUS FOR CARRYING OUT SAID PROCESS

This application is related to application Ser. No. 329,892, filed Dec. 11, 1981.

DESCRIPTION

1. Technical Field

This invention relates to a process for contactless inspection and automatic sorting of objects having constant dimensional tolerances and to an apparatus for carrying out said process. It relates more particularly to a process for contactless inspection and automatic sorting of objects presenting patterns having constant dimensional tolerances like printed circuit cards, masks, modules and integrated circuit chips used in the semiconductor domain. Said process uses the basic transformations of the mathematical morphology and of the set theory. Said invention also relates to an apparatus associated to a digital computer and provided to carry out the process of this invention.

2. Background Art

Various processes based on the comparison between a reference object meeting the appropriate requirements and a similar object to be inspected in order to check that it meets said requirements, are known in the art. In particular, the reader can be referred to the following documents:

Patent FR-A No. 74 36307 assigned to the Westinghouse Corporation and published under U.S. Pat. No. 2,249,520, describes a process consisting in scanning the reference object with an infrared radiation detector, comparing the signals generated by the reference object and by the inspected object to detect any difference between said signals and in statistically analyzing any difference to determine whether the object under inspection can be operated within the required limitations or not.

This patent also describes an apparatus including means for inspecting the reference object in accordance with a determined parameter to generate reference data by detecting said parameter, means for inspecting the object to be inspected in order to generate test data by detecting said parameter, means for comparing said reference data and said test data in order to generate compare data in relation with the difference between the reference data and the test data and means for statistically analyzing the compare data to determine the operational condition of the object under inspection.

In practice, this apparatus is provided to detect infrared radiations emitted by an electronic circuit and to analyze these radiations in order to determine whether the circuit operates correctly or not. Therefore, the basic process in use consists in selecting a reference circuit which operates correctly. The reference circuit is placed into an attaching assembly and normal bias voltages and selected input signals are applied to said reference circuit. The reference circuit surface is analyzed by a TV camera responsive to infrared radiations to generate a video signal proportional to the infrared radiation which has been emitted. The video signal is sampled and each sample is transformed into digital form to generate a first set of digital numbers, the value of each of said digital numbers being proportional to the infrared radiation emitted by a particular portion of the circuit. Then, said digital numbers are stored into a digital memory.

Then, the circuit to be inspected is placed into the attaching assembly and connected as the reference circuit to receive bias voltage and input signals substantially identical to the ones previously applied to said reference circuit. Then, the surface of the circuit to be inspected is analyzed and processed in the same way and provides a second set of digital numbers which are also stored into the digital memory.

A digital process device reads the first and second sets of digital numbers stored in the memory and compares the corresponding elements of said first and second sets to generate a third set of digital numbers. Each element of this third set is proportional to the difference between the corresponding elements of the first and second sets. Then, said third set of digital numbers is analyzed to indicate the areas where the infrared radiation emitted by the circuit under inspection is substantially different from the radiation emitted by the corresponding area of the master circuit. Substantial differences indicate that the circuit under inspection does not operate properly.

The above indicated patent describes a good example of the compare technique using a determined electrical parameter (in this case, the current flow), to compare a reference object and a similar object to be inspected. In order to compare drawing patterns by using the same principle, Patent FR-A No. 71 15069 assigned to the IBM Corporation and published under U.S. Pat. No. 2,095,523, describes an apparatus for detecting defects by optical scanning. This apparatus is mainly used for fabricating photomasks. Said apparatus can operate only if the object to be inspected shows repeated patterns. In addition, the reference object is a special object which does not belong to the family of the objects to be inspected and, therefore, which is specially built to take certain characteristics of the object to be inspected, into account.

SUMMARY OF THE INVENTION

A first object of the invention is to provide a process and an apparatus for inspecting and sorting objects showing patterns having constant dimensional tolerances allowing the operator to determine whether the object to be inspected can be operated within required limits or not, in accordance with previously determined reject criteria.

Another object of this invention is to provide a process and an apparatus for automatizing inspection and sorting of objects showing patterns having constant dimensional tolerances in order to avoid manual optical sorting.

Another object of this invention is to provide a process and an apparatus for detecting the defects of an object to be inspected from a reference object of the same family.

First of all, this invention relates to a process for automatically sorting objects showing patterns having constant dimensional tolerances. In this application, in order to make the description clearer, only the embodiment related to the sorting of ceramic modules (of the type shown on FIG. 6), is described in detail. The application of the process of this invention to other objects with constant tolerances and currently used in the semiconductor domain as masks, reticles, printed circuit cards, integrated circuit chips, can be readily ensured by the man skilled in the art. This invention mainly relates to the geometrical patterns of the objects and then it is not limited to this particular type of application.

This process mainly comprises a complex step for detecting the defects of the object to be inspected by comparing the image of the reference object (in real time or as previously memory stored in digital form) with the image of the object to be inspected. This comparison is performed by carrying out an accurate digital processing of the image involving the use of basic transformations of the mathematical morphology and of the set theory.

Both images are read, for instance in black and white with all the grey levels in accordance with an appropriate sampling frame, then quantized with sixteen levels of grey.

Then the images are threshold to appear only in black and white. For instance, the patterns to be compared are in white on a black background. This step can be performed by using a program. At last, two binary images of the reference object and of the sample object, are obtained.

Said binary images are cleaned (noise suppression) and centered and then, compared.

To detect the defects extending beyond the dimensional tolerances, it is necessary to compare the sample image with the maximum and minimum reference images.

These two images are generated by expanding and eroding (basic transformation of the mathematical morphology) the nominal reference image. Said nominal reference image is expanded and eroded in accordance with the maximum and minimum dimensional tolerances of the circuits. The tolerances are constant for the conductors of same width on all the surface of the module. The comparison of the sample image with the minimum reference image shows the defects of the "lack" type, i.e., the defects not meeting the minimum allowed dimensions.

The comparison of the sample image with the maximum reference image shows the defects of the "spreading" type, i.e., the defects exceeding the maximum allowed dimensions.

The images are compared by performing various operations of the set theory (union, intersection, etc.) which correspond to the Boolean operations (AND, OR, EXCL.OR, NOT). The compare operations as the erosion and expansion operations can be performed through the use of programs.

The analysis step performed in accordance with the reject criteria of these images, is followed by a sorting step which allows the objects showing undesired defects to be rejected.

This invention also relates to an apparatus provided to carry out the above indicated process.

The foregoing and other objects, features and advantages of the invention will be apparent from the following more particular description of a preferred embodiment of the invention, as illustrated in the accompanying drawings.

DISCLOSURE OF THE INVENTION

I. Mathematical Morphology Elements

The definitions of the various basic transformations used in digitally processing the image in accordance with the teachings of this invention are mainly based upon the principle of the structuring element and of the transformations of the "full or nil" type: i.e., erosion and expansion. The space to which the operations are applied is euclidian space R2 provided with its metric d. 0 defines the origin of the space under consideration. If B defines any set of this space, $B_x$ defines the translate of B by vector $\vec{0x}$. Then it is possible to define:

(a) expansion

A and B are two sets of R2. A new set A⊕B is said "A expanded by B" and is such that:

$$A \oplus B = \{x \epsilon R2 | B_x \cap A \neq \emptyset\}$$

In other words, a point x of space R2 belongs to set A⊕B if and only if the translate of B by $\vec{0x}$ encounters A. Set B is called a structuring element.

(b) erosion

A and B are two sets of R2. Set A⊖B is said "A eroded by B" and is such that:

$$A \ominus B = \{x \epsilon R2 | B_x \subset A\}$$

A point x of space R2 belongs to set A⊖B if and only if set $B_x$ is entirely included in A.

(c) expansion and circular erosion

In this case, the structuring element is a circle.

It is to be noted that:

$$D(x,\rho) = \{y \epsilon R2 | d(x,y) \leq \rho\}$$

said circle is a disk which has x for center and ρ for radius. In other words, a point y of space R2 belong to the disk if the distance separating this point from the center is shorter than or equal to the radius.

The distance between a point x and a set X of R2 is defined as follows:

$$d(x,X) = \inf d(x,y) \text{ with } y \in X$$

The disk with center 0 and radius $\rho$, i.e. $D(0,\rho)$ is referenced $\rho D$.

Set "X expanded by D" is such that:

$$X \oplus \rho D = \{x \in R2 | d(x,X) \leq \rho\}$$

In the same way, "X eroded by $\rho D$" can be defined such that:

$$X \ominus \rho D = \{x \in R2 | d(x,\rho) < X\}$$

(d) properties

It can be established that set "A expanded by B" is identical to the complementary set of set "complement of A eroded by B", i.e.:

$$A \oplus B = (A^c \ominus B)^c$$

All these transformations of the "full or nil" type are iterative. Then, it is possible to define two other operations.

| An opening operation i.e.: | it is an erosion followed by expansion (A ⊖ B) ⊕ B and |
|---|---|
| A closing operation i.e.: | it is an expansion followed by an erosion (A ⊕ B) ⊖ B |

These last transformations will be used to clean the images.

In general, an erosion suppresses the portions of the image which are smaller than the structuring element. (Therefore, it is the same for the expansion over $A^c$).

An opening operation suppresses all the portions of A which are smaller than the structuring element without modifying the remaining portion of the image. (A closing operation has the same effect on $A^c$).

II. Digitally Processing of the Image

Figure 1:
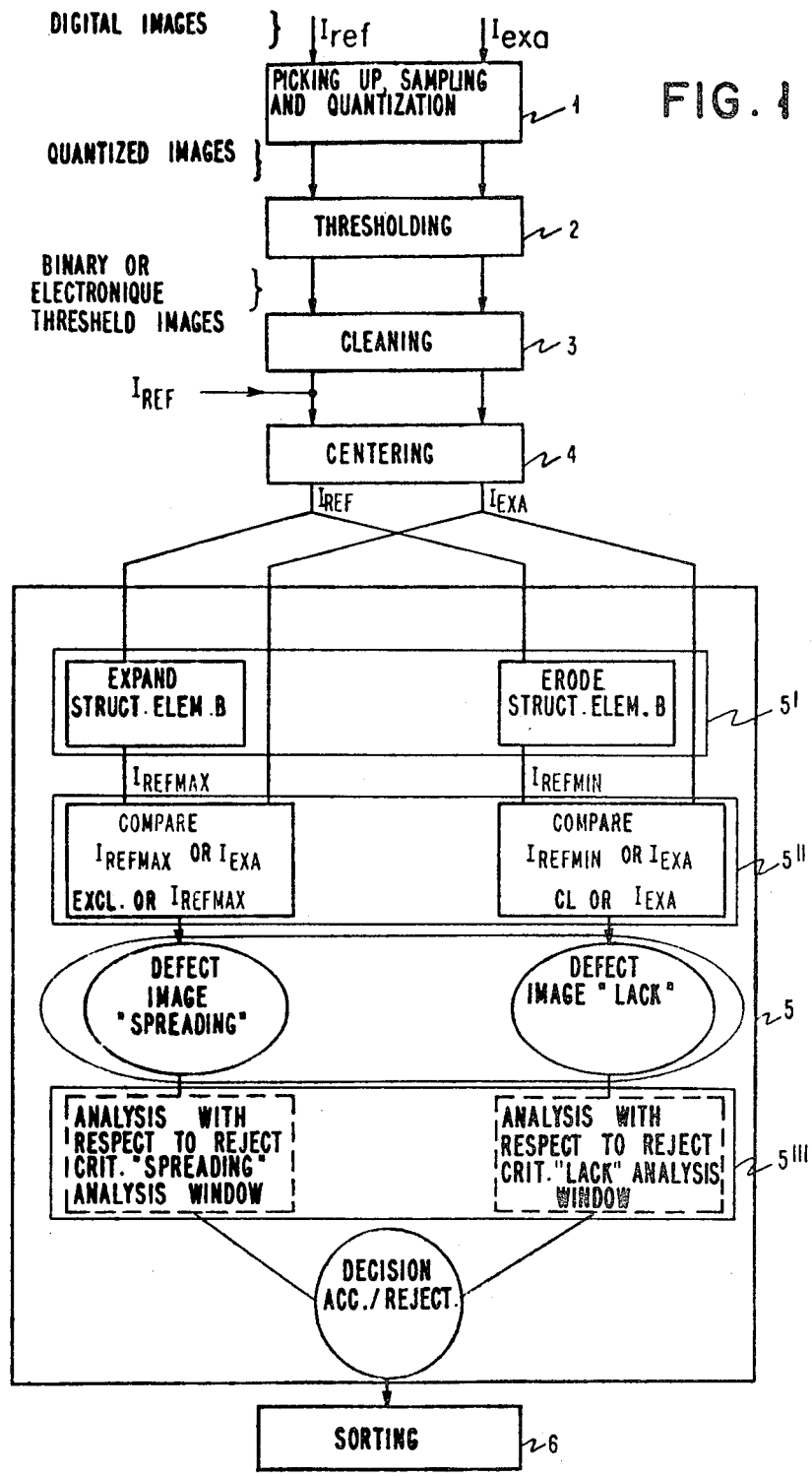
FIG. 1 is a flowchart representing the various steps of the inspection and sorting process of this invention.

The various basic steps which are described below are shown in the flowchart of FIG. 1 and bear reference numbers 1 to 6.

1. Picking up, sampling and quantizing the image

The images of the reference object ($I_{ref}$) and of the object to be inspected ($I_{exa}$) provided by the pick up device are, for instance, in black and white with all the grey levels. First of all, these analog images are sampled according to an hexagonal or square frame, for instance. The signal amplitude is quantized for each point of the image and this information is coded over four bits. The image lines can comprise a variable number of bits in accordance with the various applications. In general, 1024 or 2048 lines of 512 to 2048 bits are satisfactory in most cases. In this application, 2048 lines of 2048 bits have been chosen, i.e., with a 2.54×2.54 cm module, one has a pitch of 12.5$\mu$ between two images points (pixels), i.e., four millions of points to be processed.

2. Thresholding

Only the geometry of the object patterns is taken into account in the automatic processing of defects. Therefore, this leads to process binary images obtained after thresholding.

Any point of the image showing a level of grey exceeding a certain threshold, will be made equal to 1. Below said threshold, any point of the image will be made equal to 0. This step allows binary images in black and white to be obtained. The problem which appears relates to the detection of the correct threshold for the objects to be analyzed.

Figure 2:
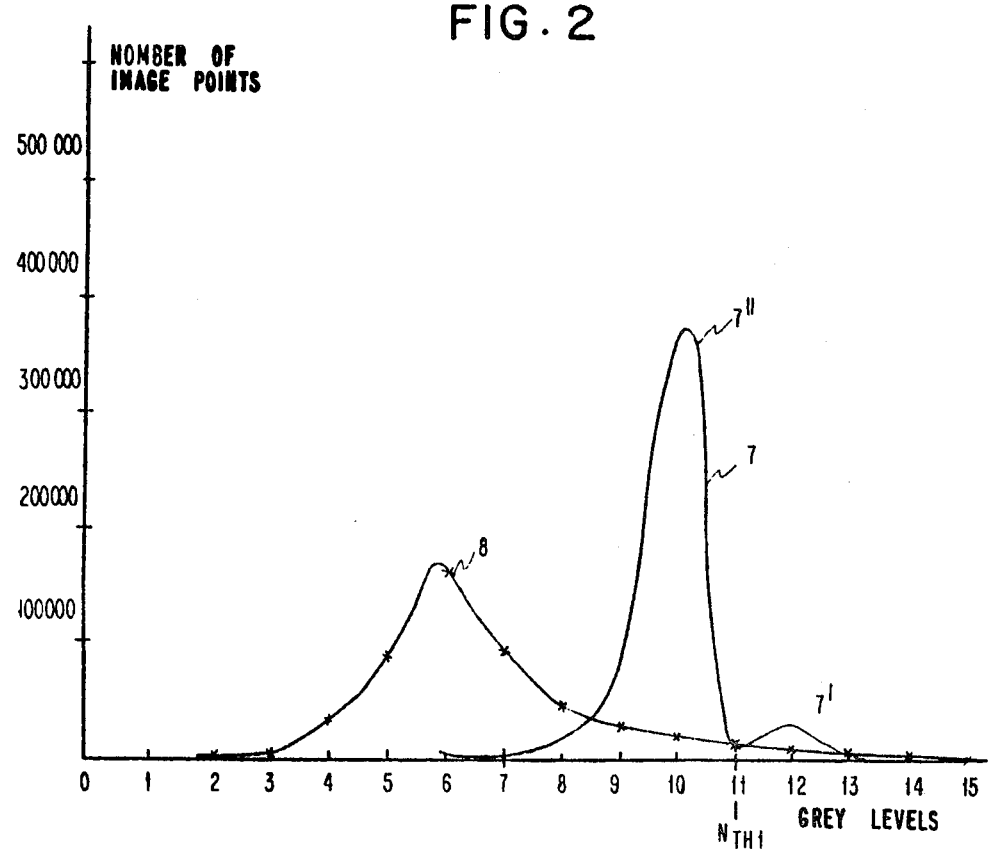
FIG. 2 is a frequency curve representing the distribution of the "image" points (pixels) according to the signal amplitude for two images, the first image being very contrasted and the second one not very contrasted, both images being in black and white with sixteen levels of grey.

An appropriate thresholding technique based upon the construction of the image frequency curve is described below while referring to FIG. 2. For the image with 16 levels of grey and well contrasted, the frequency curve show two peaks or modes which are well differentiated (7' and 7") and represented on curve 7 of FIG. 2. Peak 7' shows the distribution of the object patterns while peak 7" shows the distribution of the image background. To detect the correct threshold, it is sufficient to choose value $N_{TH}$ of the threshold corresponding to the valley between the two peaks. As to the example of curve 7, one has $N_{TH}=11$. Thus, all the points of the image which has been analyzed and which show a level of grey exceeding 11, will be provided with a binary 1 value while all the other points will be provided with a binary 0 value.

When contrast decreases (in other words, when the image background shows a gradient of greys), the valley between the two peaks becomes less deep and it becomes difficult to choose the optimum threshold. Thus, for the not or not very much contrasted images, the threshold can be chosen in various ways, in particular by processing the images region by region. The threshold of each region is detected from its histogram. Then, the resulting thresheld image is comprised of all the thresheld regions. A frequency curve characterizing such a not very much contrasted image is given by curve 8 of FIG. 2. In this case, the experiment shows that threshold value $N_{TH}$ can be chosen equal to 7. In all the cases, a program can be used for automatically detecting the threshold through the analysis of the frequency curve of the intensities of the image points of the image which is analyzed.

Various techniques including the above-indicated ones, are described in the article entitled: "A Survey of Edge Detection Techniques" of Larry Davis published in "Computer Graphics and Image Processing" (1975), 4, pages 248–270 and more particularly in the portion relating to the article of C. K. Chow.

3. Cleaning

Cleaning is performed by erosion to suppress all the image points related to noise. The size of the structuring element which is going to erode the image should be smaller than the size of the smallest defect which is to be detected. The portions smaller than the erosion size disappear while the other ones remain and will be subsequently reconstructed by an expansion of the same size. Finally, this operation is of the opening type. It would have been possible to obtain the same result by performing an operation of the closing type or better, by combining both types. The expand operation is carried out in a symmetrical way: the complementary image of the frame is eroded and the result complement is taken out as indicated in the following relation:

$$A \oplus B = (A^c \ominus B)^c$$

Also, cleaning can be performed after the centering step. At last, this step is optional and depends on the image quality.

In practice, for carrying out these mathematical morphology operations as erosion and expansion, various structuring elements can be chosen and, more particularly, in accordance with the frame in use. On the image sampled in accordance with the hexagonal frame, it is possible to choose the hexagon form which is the structuring element the closest to the circle.

Let us assume that one has a hexagon of size n and that the product of the sampling pitch by n represents the circle radius. In this case, for a size 1 erode operation for instance, all the image points are structured by the structuring element which will be a hexagon of size 1. All the apexes of the hexagon as well as its center, are made equal to 1. The hexagon is centered on the point to be analyzed. If the hexagonal vicinity of each point as well as the point itself, coincide with the values given to all the apexes of the hexagon (center included), then the initial point takes a binary 1 value. If not it takes a binary 0 value. In other words, any binary point equal to 1 provided with at least an adjoining point equal to 0, is suppressed from the image while the binary points equal to 0 keep their value. Therefore, the image has been submitted to a transformation of the "full or nil" type.

If a square frame is in use, it is possible to use a cross shaped structuring element and the same process is carried out. The size and the pattern of the structuring element can vary in accordance with the type of the application. In this description, only the square frame and a single cross shaped structuring element will be used to provide a better understanding of the invention. The number of the image points (pixels) varies from 500,000 to 10 millions or more, according to the various applications.

4. Centering

Before comparing the reference image with the sampled image, it is necessary to recenter both images in space. This operation must be automatic and can be program controlled. Various techniques for centering or aligning masks are well known by the man skilled in the art (for instance, by using flags or reference marks), can be used. An appropriate recentering technique is described below while referring to FIG. 3.

Figure 3:
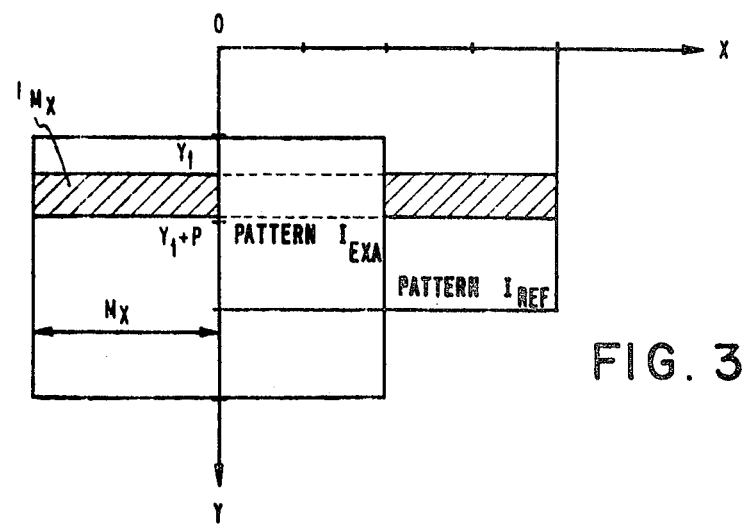
FIG. 3 shows a pattern of the image of the reference object and a pattern of the image of the object to be inspected, both patterns must be centered.

Two patterns are schematically shown on FIG. 3. A pattern belongs to reference object image $I_{ref}$ and the second pattern belongs to sample object image $I_{exa}$. The second pattern is not aligned with the reference image pattern. These patterns can consist in portions of flags or reference marks which are in current use for aligning masks, modules, etc.

A program allows the offsetting between the images on axis x and y, to be calculated.

To calculate this offsetting on axis x which is represented by $M_x$, it is sufficient to take some successive lines y (from a determined line $y_1$) crossing both images and to calculate hachured surface $I(M_x)$. FIG. 3 shows that the more $I_{ech}$ is offset to the right (by steps on axis x), the smaller is surface $I(M_x)$. Said surface tends to a minimum when maximum recentering on axis x is attained.

To carry out a faster calculation, the program computes only a limited group of p lines for the offsetting on axis x and of q columns for the offsetting on axis y.

The parameters ($y_1$ and p, as to the offsetting on axis x) are chosen at the program entry. Therefore, this program consists in analyzing function $I(M_x)$ which represents the hachured surface according to the different values of offsetting $M_x$ (offsetting on axis x between both images).

Then, the program automatically determines value $M_x$ at a minimum of function $I(M_x)$.

The same process is carried out for the offsetting on axis y by taking vertical lines parallel to axis Oy, which leads to determine $I(M_y)$ and $M_y$ by using corresponding parameters ($x_1$,q).

Figure 4:
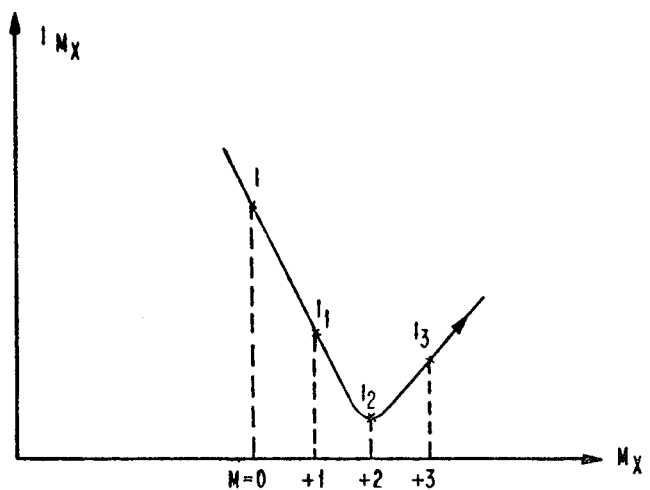
FIG. 4 shows curve I(Mx) representing the hachured area shown on FIG. 3 and which is proportional to offsetting Mx of the patterns and its variation in function of the displacement of the object to be inspected.
Figure 5:
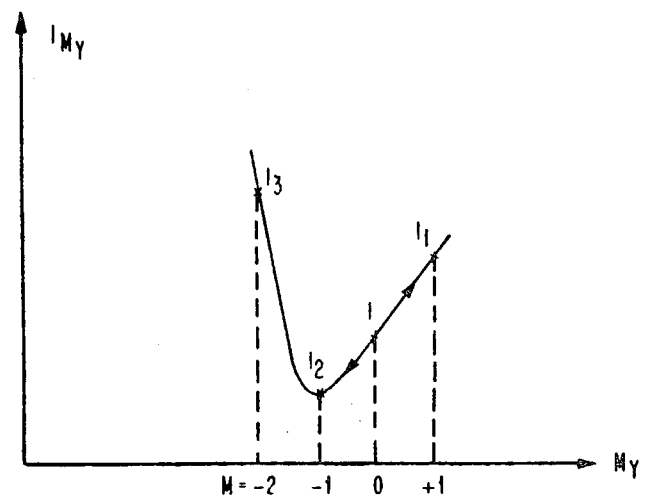
FIG. 5 is a similar representation of curve I(My).

When taking the pattern shown on FIG. 3 as an example, the result of these logical operations appears as the curves shown on FIGS. 4 and 5. These figures show $I(M_x)$ and $I(M_y)$ which indictate the minima for certain values of M. FIG. 4 shows that function $I(M_x)$ decreases from initial value I by taking values $I_1$, $I_2$, before increasing and taking value $I_3$ (for determined values $y_1$ and p) for different values of $M_x$ when $I_{exa}$ has been offset to the right by successive steps. The minimum of $I(M_x)$ is obtained for two steps. Then it is necessary to move $I_{exa}$ by two steps to the right.

Figure 6:
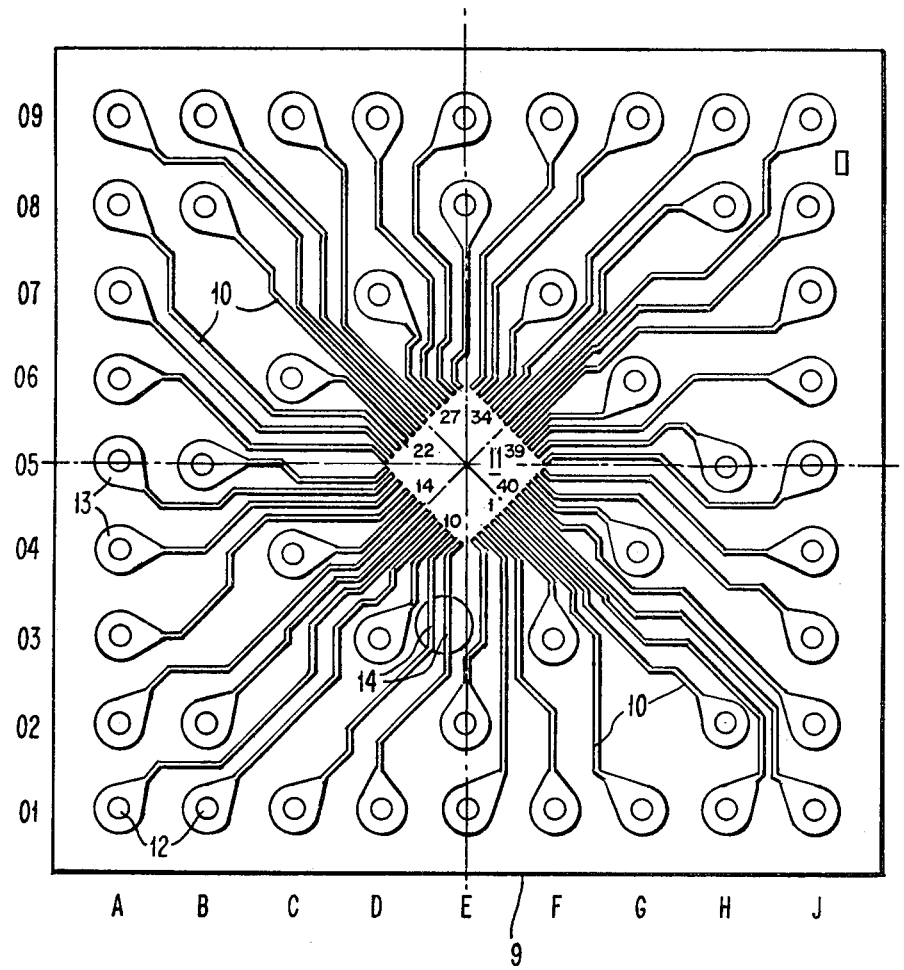
FIG. 6 shows a constant width conductor arrangement on the surface of a 48-pin ceramic module provided to receive a single integrated circuit chip.

In the same way, FIG. 6 shows $I(M_y)$ and that a first attempt $I_1$ to the right is made in the wrong direction since $I_1 > I$, then to the left.

Therefore, the minimum is obtained for a step towards the negative values of y.

This recentering step can be easily program controlled.

It should be understood that in some applications, recentering can be performed either in plane (x, y, $\theta$) or in space (x, y, z).

Since only a portion of the image is chosen, it is necessary to check that these lines effectively cross the patterns of the object under analysis as far as both the sample and the reference images are concerned and not only the background. The choice is readily made from the reference image which is known at the beginning and which allows these parameters ($x_1$, $y_1$, p, q, ...) to be determined. In addition, in order to obtain the desired results from the offsetting calculation, it is necessary that each pattern of $I_{ref}$ overlaps the corresponding pattern of $I_{exa}$. This can be ensured through an approximate centering operation performed when picking up the images. After having successively picked up, sampled, quantized, thresheld, cleaned and centered the images, the binary images resulting from the reference object is reference $I_{REF}$ and the binary image resulting from the object to be inspected is reference $I_{EXA}$.

5. Showing defects

In the semiconductor integrated circuit industry, it is known that the objects to be compared consist essentially in masks (reticles), integrated circuit chips and electronic modules. In every case, there are dimensional tolerances about some patterns of these objects. For instance, in the modules, the width of the conducting lines is provided with dimensional tolerance.

The topology of a current module 9 is shown on FIG. 6. This module is a ceramic substrate which bears a pattern of conducting lines 10 electrically connecting the contact balls of a chip provided in 11 and pins (not shown) provided in holes 12. The conducting lines are wider at the pins to form contact pads 13. The conducting lines and the contact pads show constant dimensions on all the surface of the substrate as shown on the figure.

The dimensional tolerances of these conducting lines are known and indicated in the manufacturing and inspection instructions and, of course, vary in accordance with the objects to be analyzed.

Some dimensional tolerances are constant on all the object to be analyzed (it is the case of the module shown on FIG. 6). Some others vary in accordance with the location of the patterns on the object (it is the case of some modules). Further, it has been noted that two main types of defects appear on the module: (1) the defects of the "lack" type, the "lack" being what is missing on the image of the module to be inspected with respect to the image of the reference module, and (2) the defects of the "spreading" type, the "spreading" being what is added on the image of the module to be inspected with respect to the image of the reference module.

Figure 7:
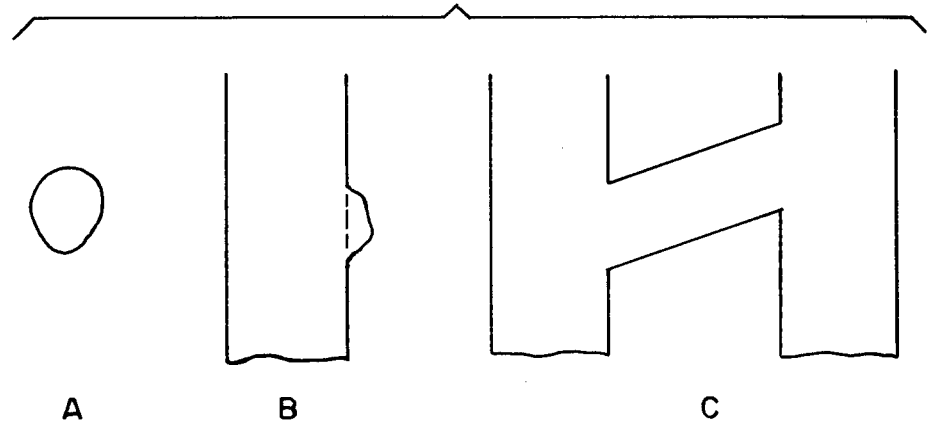
FIG. 7 shows various defects of the "spreading" type.
Figure 8:
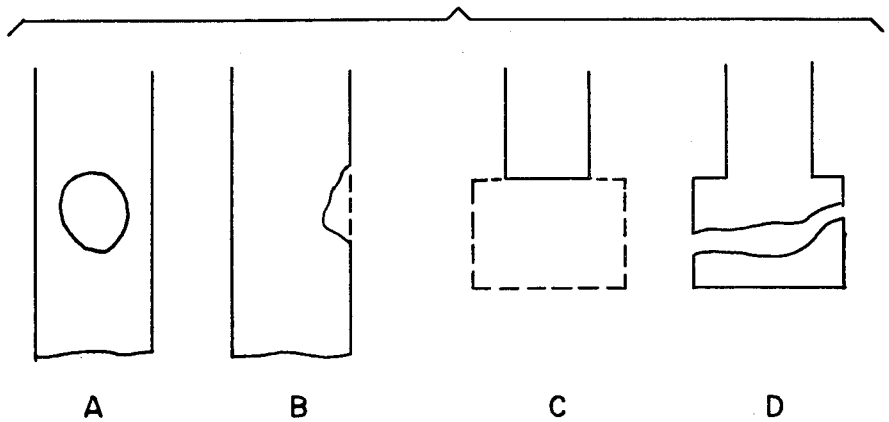
FIG. 8 shows various defects of the "lack" type.

In this domain, the defects can have various shapes some of which among the most typical ones, are shown on FIGS. 7 and 8.

(1) Defects of the "spreading" type
They are of three main sub types:
(A) the "island" sub type (parasitic pattern)
(B) the "spreading along a pattern" type
(C) the "bridge" type (between two patterns)
Parts A, B and C respectively represent defects on FIG. 7.
(2) Defects of the "lack" type
They are of four main sub types:
(A) the "hole" type (a hole in a pattern)
(B) the "cut out" type
(C) the total lack of a pattern
(D) the "break" type (a broken pattern).
Parts A, B, C and D respectively represent these defects on FIG. 8.

In this application, only objects with constant tolerances are considered. It is the case of the module shown on FIG. 6. In these relatively simple conditions, there are only two reject criteria to be applied: the criterion relative to the defects of the "lack" type and the criterion relative to the defects of the "spreading" type. A map or an image of the defects will be established for each type of defect by processing differently images $I_{REF}$ and $I_{EXA}$ to be compared.

To determine the defects of the "spreading" type while taking the maximum allowed width into account, $I_{REF}$ is expanded to the size of the dimensional tolerances, which gives $(I_{REF})_{max}$, then $(I_{REF})_{max}$ is compared to $I_{EXA}$ by performing the following complex logical operation:

$$[(I_{REF})_{max} \text{ OR } I_{EXA}] \text{ EXCL. OR } (I_{REF})_{max}.$$

If the resulting set or defect image is not empty, this indicates the presence of defects of the "spreading" type. This logical operation is chosen because it allows the defects of the "spreading" type to be especially selected. As to the defects of the "lack" type, $I_{REF}$ is eroded to the size of the dimensional tolerances, which gives $(I_{REF})_{min}$. Then $(I_{REF})_{min}$ is compared to $I_{EXA}$ by performing the following complex logical operation:

$$[(I_{REF})_{min} \text{ OR } I_{EXA}] \text{ EXCL. OR } I_{EXA}.$$

If the resulting set or defect image is not empty, this indicates the presence of defects of the "lack" type. This logical operation is chosen because it allows the defects of the "lack" type to be especially selected. It should be noted that, in this embodiment, structuring element B of the expanding and eroding operations is identical for both operations since the minimum and maximum dimensional tolerances are equal. If they are different, structuring elements of different sizes are to be used.

Other logical operations can be performed, in particular if only one defect image is desired. Therefore, two defect images are obtained at last (see FIG. 1). One image showing the "spreading" defects and the second one showing the "lack" defects.

Figure 9:
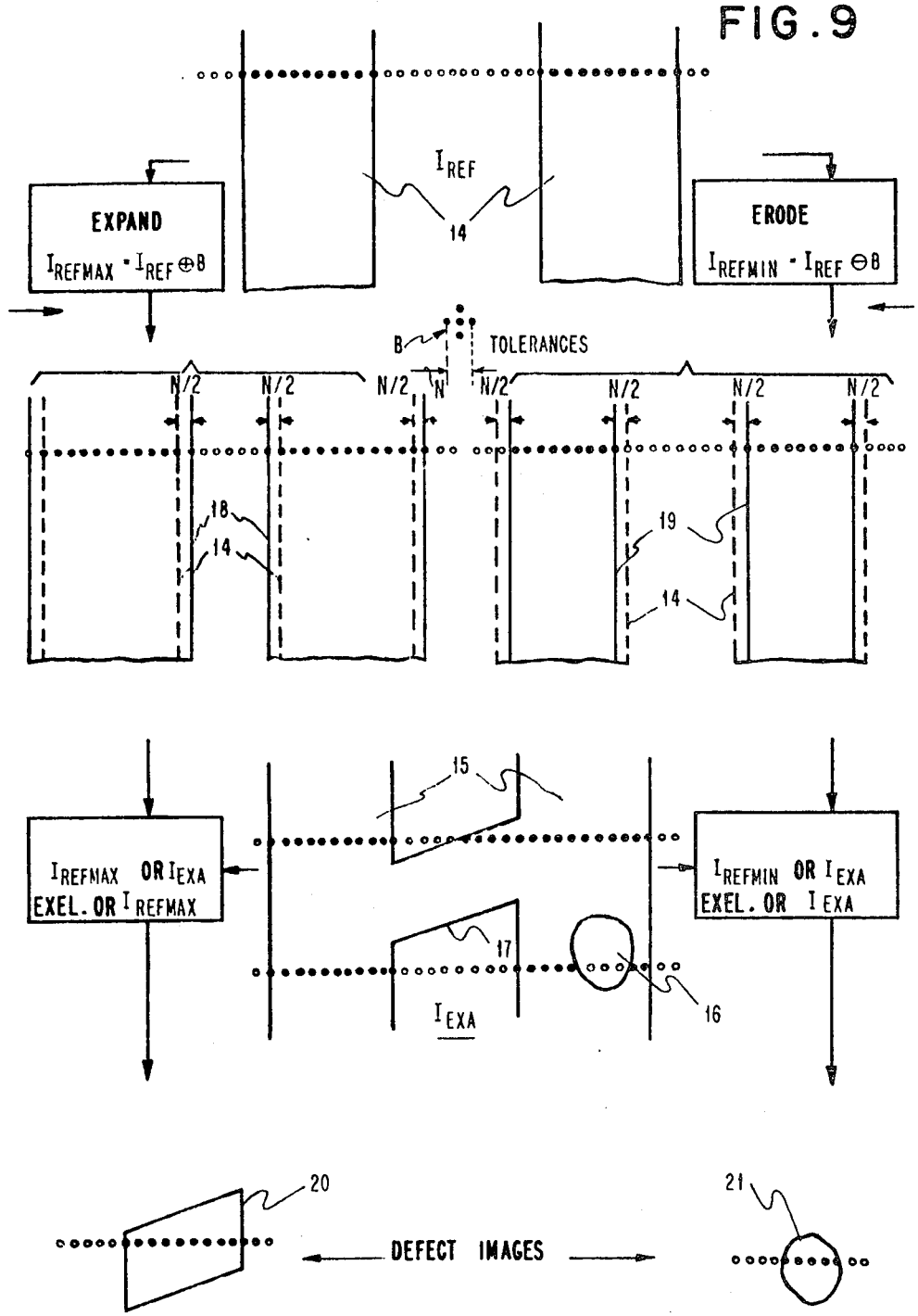
FIG. 9 shows the various transformations and logical operations applied to the images of the reference object and of the object to be inspected to obtain images of the defects of both types.

Said step 5 showing defects will be briefly described while referring to FIG. 9. This figure shows a reference image $I_{REF}$ which represents, for instance, a portion 14 of two conducting lines 10 of module 9 shown on FIG. 6. It is also shown in image $I_{EXA}$ of the module to be inspected provided with the two corresponding conductors 15 but which shows with respect to $I_{REF}$ both a lack (hole) 16 and a spreading (bridge) 17, i.e., a defect of each type. Since digital images are concerned, the pixels are represented by small circles. Therefore, the black circles show the effective image points corresponding to binary ones. First, images $(I_{REF})_{max}$ and $(I_{REF})_{min}$ which are, respectively, the "expanded" and the "eroded" images of the reference image, are formed by a same structuring element B the size of which corresponds, in this case, to the maximum and minimum dimensional tolerances $\pm N$ allowed for these lines. In the example depicted on FIG. 9, one has chosen a pitch or an interval between two pixels of $N/2=12.5\mu$. It is approximately shaped as a symmetrical cross. After processing, the lines are respectively referenced 18 and 19.

The following operation consists in carrying out a comparison in accordance with complex logical operators. First, one has:

$$[(I_{REF})_{max} \text{ OR } I_{EXA}] \text{ EXCL. OR } (I_{REF})_{max}$$

which makes defect 20 of the "bridge" type to appear and then:

$$[(I_{REF})_{min} \text{ OR } I_{EXA}] \text{ EXCL. OR } I_{EXA}$$

which makes defect 21 of the "hole" type to appear.

It is to be noted that it is possible to combine the two defect images on a single image by performing an OR operation.

It should be also noted that it would have been possible to compare $I_{REF}$ and $I_{EXA}$ during a preliminary operation. The lack of defects would have meant that the object to be inspected was identical to the reference object.

The last operation of step 5 consists in analyzing the defect images in accordance with their proper reject criteria. In the case of objects with constant dimensional tolerances, these criteria consist in the allowed dimensions of the defects. In practice, it is just as generating an analysis window and comparing each defect with this window. The shape, location and nature of the defects are not taken into account. In this case, the reject criteria are, then, very rough and can be identical for both the "lack" and the "spreading" types of defect.

Thus, processing step 5 mainly includes a first operation 5' for adjusting the pattern of $I_{REF}$ to the dimensional tolerances (expansion and erosion), a second operation 5" for comparing $I_{REF}$ with $I_{EXA}$, which provides two defect images ("lack" and "spreading" types of defect) and at last, a third operation 5''' for analyzing defect images in accordance with predetermined reject criteria.

Thus, the modules are very quickly analyzed. In manufacturing modules, it appears that the percentage of modules showing defects is relatively small, for instance, under 5%. The modules showing defects and which are rejected at this level, can be more accurately inspected or re-examined by carrying out an additional step for recognizing and analyzing the defects.

In effect, some defects can be accepted as long as they are considered as not detrimental to the module reliability. This additional step is very important since the cost of the modules is very high and is described in European patent application No. 80430030.9 filed on Dec. 18, 1980.

6. Sorting

The objects without any defect or with acceptable defects according to the reject criteria, are accepted at this level. Having identified those objects which have no defects or acceptable defects, one skilled in the art will appreciate that any number of automatic sorting apparatus is available in the art for performing this sorting step once a reject or non-reject condition has been indicated.

III. Apparatus for Applying the Above Described Process

The process for digitally processing images of the reference object and of the object to be inspected as described in part II of this application, can be applied in various domains as indicated above and more particularly, in the semiconductor domain in which it can be more particularly used for automatically sorting printed circuits, modules, masks and semiconducting chips (metallurgy inspection), some patterns of which as the conducting lines, are provided with constant dimensional tolerances. As to the masks and modules, the images are very contrasted (practically black and white). In this case, the automatic threshold detection can be carried out without any difficulty as well as the recentering operation.

Figure 10:
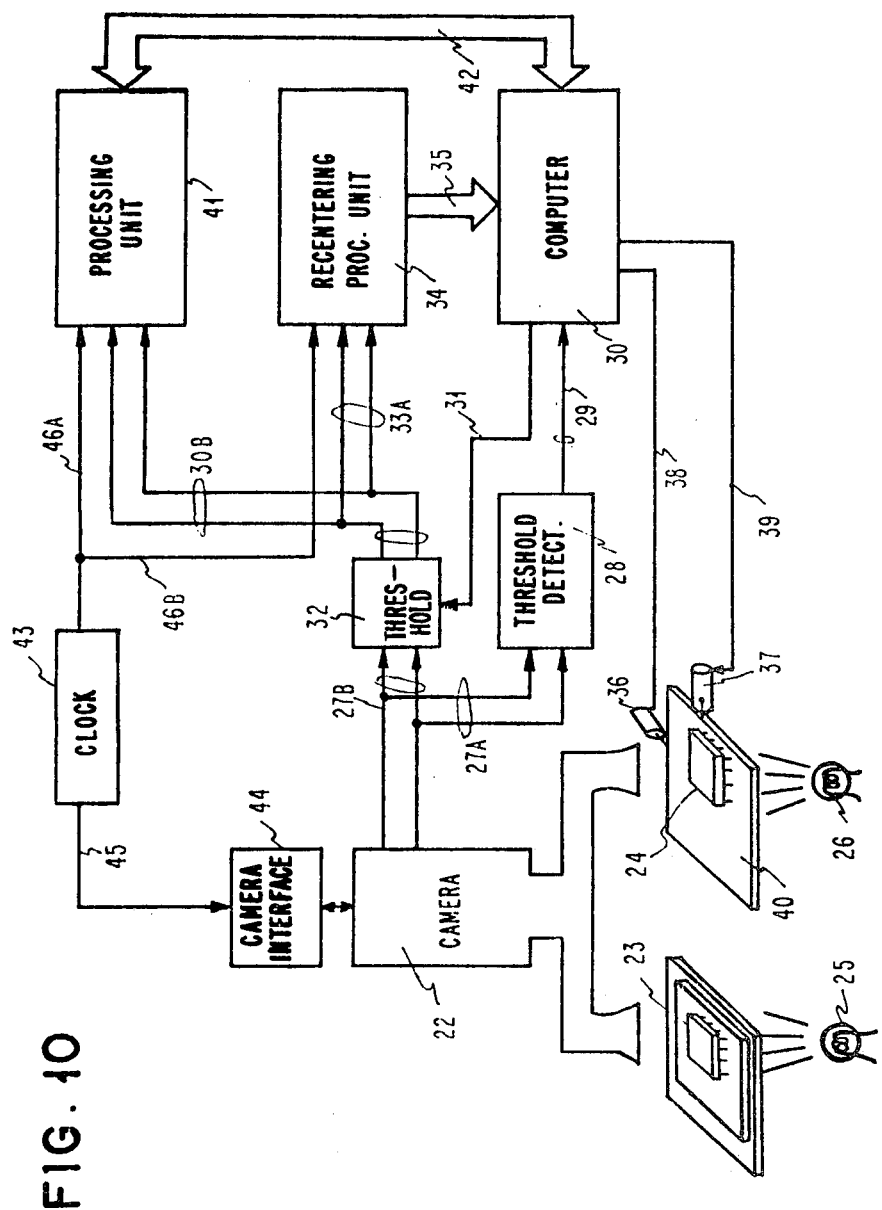
FIG. 10 is a schematic diagram which shows the various components of the apparatus of this invention.

A first embodiment of the invention and an appropriate apparatus given as an example, will be described below while referring to FIG. 10.

Various types of pick up devices can be used in accordance with the nature of the objects to be sorted. An electron microscope can be absolutely necessary to inspect chips and masks ($1 \times$). A single camera or a photodiode array or a charge coupled device can be sufficient for reticles ($10 \times$) or modules. The latter application has been retained in this description. A current module of $2.5 \times 2.5$ cm is provided with a pattern of conducting lines of a constant width of $125\mu$ with an allowed tolerance N of $25\mu$. This means that a conducting line is accepted when its width L meets the following requirement $100\mu \leq L \leq 150\mu$. With a camera of 2K bits, the distance between two pixels is of about $12.5\mu$. Structuring element B of FIG. 9 is perfectly appropriate since allowed tolerance N is also of $25\mu$. For the modules with conductors having a width exceeding $125\mu$, for instance $250\mu$, the most appropriate multiple of $25\mu$ is to be chosen. In every case, it is possible to choose a camera with the most appropriate resolution.

The pick up device consists in a digital color camera 22 with a resolution of 10 bits (vidicon tube). Reference object 23 and object to be inspected 24 are illuminated by two sources of different colors (red and blue) 25 and 26. Two lenses provide two images to be compared while a set of prisms (not shown) superimposes said two images on the camera lens. Therefore, both images are picked up in the same time by the color camera which separates the two signals of different colors at the output.

This apparatus has the advantage of retaining the 10 bits of resolution while being independent from the thermal drift of the camera, from the defects of the vidicon tube as well as from the optical aberrations.

After having been separated, the digital signals issued from the camera are transmitted through bus 27A to a threshold detect block 28 where they are analyzed. Block 28 establishes the intensity histograms of both images (grey distribution) and supplies them through bus 29 to computer 30 which determines the respective thresholds of images $I_{ref}$ and $I_{exa}$. Then these values are applied through bus 31 to the input of threshold block 32 which also receives the signals emitted by the camera through bus 27B. The images are thresheld at the output of block 32: each image point takes a binary "0" or "1" value after having been compared to the threshold. Both thresheld binary images are provided through bus 33A to unit 34 recentering said images along axis x and y and possibly, along axis $\theta$. With the above described process (II. 4), this unit computes surfaces I(M) of the non-overlapping area of the two images when they are offset. Information is transmitted through bus 35 to computer 30 which controls stepping motors 36 and 37 through lines 38 and 39 to move support 40 of the object to be inspected, while analyzing the results of the recentering block until optimum recentering is obtained, which corresponds as seen above, to the minimum of functions I(M) (along axis x and y).

To ensure a faster calculation, the program chooses only a group of eight lines for the offsetting along x (p=8) and of eight columns for the offsetting along y (g=8).

Then, processing unit 41 receives through bus 30B, information corresponding to recentered images.

This unit ensures the various above indicated logical operations, from prewired circuits.

This unit is schematically comprised of two assemblies: a first assembly for analyzing the "lacks" and a second assembly for analyzing the "spreadings".

In addition, it measures the horizontal and vertical projections of the defect and its location. It contains the "erode" and "expand" blocks. This unit analyzes and compares the images in accordance with the process described on FIG. 1 and transmits the result to computer 30 through a line of bus 42: i.e., the object to be inspected is "accepted" or "rejected". The assembly is driven by a clock 43 (for instance 10 MHz) which controls interface circuit 44 of the camera, processing unit 41 and recentering calculation unit 34 through lines 45 and 46A and B, respectively. The circuits comprising processing unit 41 are more particularly shown on FIGS. 11A to 11D. FIG. 12 shows a block diagram of the processing unit.

Figure 11A:
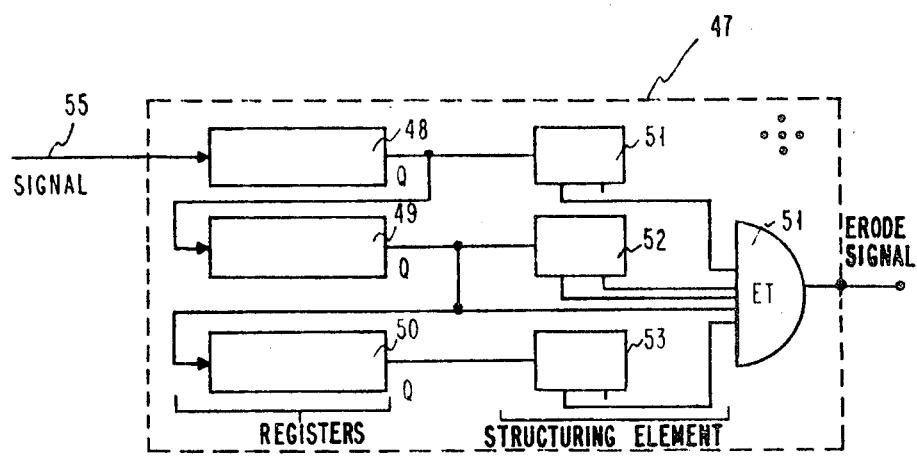
FIGS. 11A, B, C and D schematically show the various logical circuits used in the processing unit.
Figure 12:
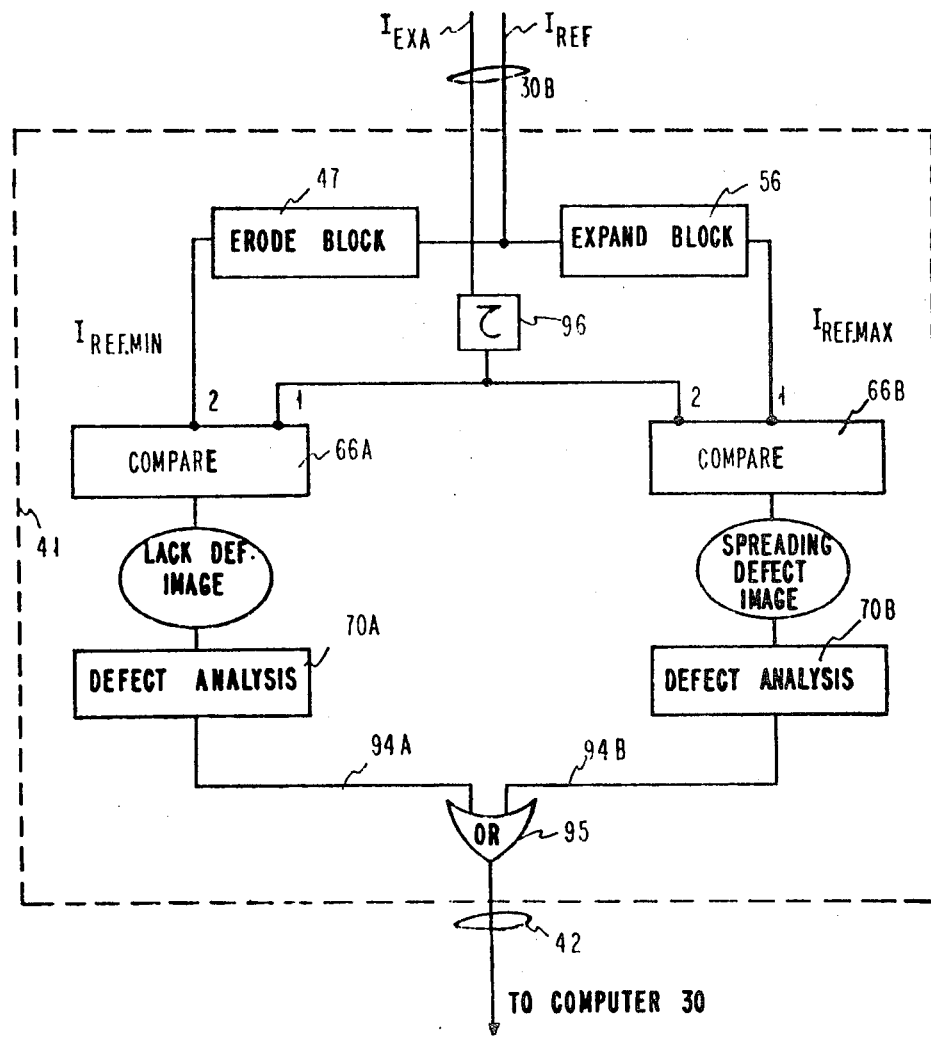
FIG. 12 is a schematic diagram of the processing unit.

FIG. 11A shows erode block 47 which is comprised of three main sections: a memory section comprised of shift registers provided with two outputs Q and $\overline{Q}$, a section for generating structuring element B shown on FIG. 9 and an AND gate. The number of registers is function of the number of lines to be stored. In the example, of the above indicated cross-shaped structuring element, three lines are to be stored. Therefore, three shift registers 48, 49 and 50 are provided. The capacity of these registers depends, of course, on the number of the bits representative of the line: 1024 or 2048 bits, for instance. Therefore, since a cross-shaped structuring element is chosen, three 2-bits shift registers 51, 52 and 53 are necessary. These registers are of the parallel output type. This means that the bits can be directly accessed in the register. The two outputs of register 52 are used since three points (the transverse beam of the cross including its center) are to be compared while only one output is required for each register 51 and 53 which compare each only one point (the upright of the cross excepted the center point already included in the transverse beam of the cross). At last, the erode block comprises an AND gate 54. The system operates as follows. The input binary signal representative of the image of reference object $I_{REF}$ is applied into the erode block through line 55. The binary data fill up first register 48, then, line by line, the other registers. Registers 51, 52 and 53 of the structuring element operates all the time as a window. AND circuit 54 outputs a "1" only for the points corresponding to $(I_{REF})_{min}$. In effect, for these points and only for these points, outputs Q of registers 48, 49 and 50 on the one hand and the useful contents of registers 51, 52 and 53, on the other hand, are at level 1 ("1" represents the presence of an image point). Therefore, the eroded input signal appears at the output of block 47. It is obvious that in accordance with the number and the nature of the registers as 51, 52 and 53 and the wiring of the AND gate, it is possible to obtain structuring elements of various shapes (an hexagon on an hexagonal frame, a square or a cross on a squared frame, ... ). Therefore, this block elaborates image $(I_{REF})_{min}$ as shown on FIG. 9 (conductors 19).

Figure 11B:
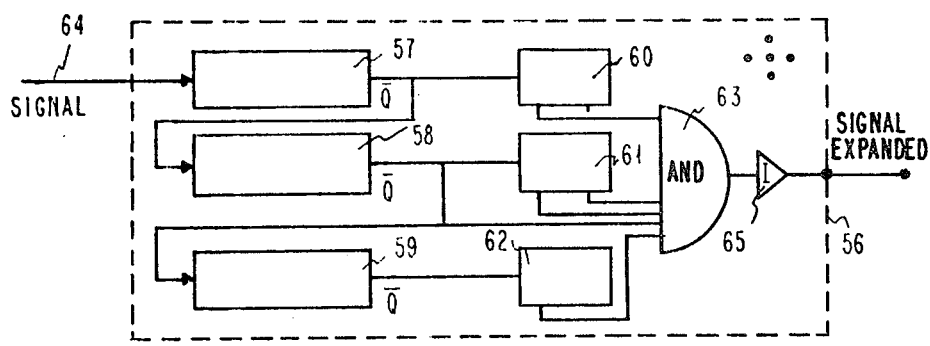

Expansion block 56 shown on FIG. 11B is similar to erode block 47. Therefore, from the above indicated relation (see I. d), it can be deduced that the "expand" function is equal to the complement of the image complement after being eroded.

Therefore, this time, one uses the inverted output $\overline{Q}$ of three shift registers 57, 58 and 59 identical to registers 48, 49 and 50 and three 2-bits shift registers 60-61-62. Wiring of AND gate 63 is also identical. Therefore, AND gate 63 outputs the erode function of the inverse of the signal appearing on line 64 and through the action of invert circuit 65, the output signal is really the expand function of the input signal. By applying $I_{REF}$ as an input signal, signal $(I_{REF})_{max}$ is obtained at the output of block 56.

Of course, circuits 47 and 56 can be used to perform cleaning step 3. It is sufficient to determine the appropriate structuring element corresponding to the smallest acceptable defect at the level of the electronic images, as described above.

Figure 11C:
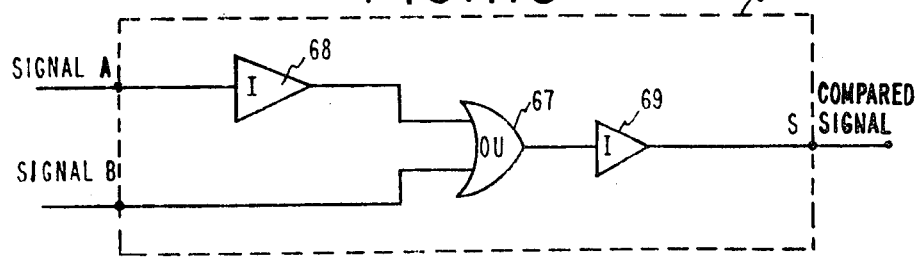

FIG. 11C shows an example of a circuit 65 able to perform the following operation: (SIGNAL A OR SIGNAL B) EXCL. OR SIGNAL B between input signals SIGNAL A and SIGNAL B, which is the basic operation of the comparison indicated in step 5 of FIG. 1. Circuit 66 includes an OR circuit 67 receiving on the one hand, signal A which has been previously inverted in invert unit 68 and, on the other hand, signal B. The resulting signal is again inverted in invert unit 69. Therefore, the output signal is as follows:

(SIGNAL/ OR SIGNAL B)=(SIGNAL A) AND (SIGNAL/ )

This expression can also be written as follows:

(SIGNAL A OR SIGNAL B) OR EXC. (SIGNAL B).

If the signals representative of $I_{REF\,min}$ and $I_{EXA}$ are applied to block 66, the signal representative of the "lack" type defects can be found by satisfying the following relation:

SIGNAL A=$I_{REF\,min}$ and SIGNAL B=$I_{EXA}$.

In this case, compare block 66 will be referenced 66A.

In the same way, the signal representative of the "spreading" type defects, can be obtained by satisfying the following relation:

SIGNAL A=$I_{EXA}$ and SIGNAL B=$I_{REF\,max}$ and the compare block will be referenced 66B.

FIG. 11D shows a circuit 70 able to perform the analysis operation as indicated in FIG. 1 (step 5). For a better understanding of the invention, it is assumed that the reject criterion is the same whether the defects are of the "lack" type or of the "spreading" type. In this example, it is admitted that the smallest acceptable defect will have a projection of four image steps (pixels) either on axis X or on axis Y. Consequently, the circuit is able to detect a defect only from a projection of five steps. In this case, the analysis window is of 5×5 pixels. Five signal lines of the defect image will be stored into shift registers 71 to 75 (only the last bit of which can be accessed), which respectively drive five 5-positions registers 76 to 80, each position being able to be accessed. Positions A1 to A5, B1 to B5, etc. ..., of registers 76, 77, etc. respectively drive OR circuits 81, 82, etc. The outputs of these OR circuits are applied to the inputs of an AND gate 86. If at a given moment there is at least one line of the defect image which comprises five image points (i.e. five "1" bits), the arrangement allows AND circuit 86 to go to the "1" level and to indicate that there is a defect which has a length along axis X which equals or exceeds 5 pixels and that the object is to be rejected. The same information can also be obtained about axis y from AND gate 87 which is driven by OR circuits 88 to 92 operating in the same way as OR circuits 81 to 85. OR circuit 88 collects positions A1, B1, C1, D1, E1, i.e., five positions on axis X. Objects showing defects as referenced in 20 and 21 on FIG. 9, would, therefore, be rejected with this criterion. In effect, defect 20 shows that it has a maximum length of 11 pixels on axis X while defect 21 shows 6 pixels on axis Y. Signals SX and SY issued from AND gate 86 and 87 drive an OR circuit 93. Therefore, the presence of an unacceptable defect is indicated by line 94 when it is at the high level. When defect analysis block 70 processes the signals issued from the image of the defects of the "lack" type, it will be referenced 70A (output line 94A) and when it processes the signals issued from the image of the defects of the "spreading" type, it will be referenced 70B (output line 94B). At last, it can be noted that more complex analysis windows can be considered by the man skilled in the art in accordance with various applications.

It is obvious that all the registers shown on lines 11A to 11D are driven by clock 43.

FIG. 12 is a block diagram of processing unit 41 (the interactions with clock 43 are not shown) which ensures all the operations appearing in block 5 of FIG. 1 (and possibly, in addition, the cleaning step of block 3). The processing unit is also controlled by computer 30 which receives from said processing unit through bus 42, the decision elements about the object to be inspected (sorting step, block 6, FIG. 1). The circuits which are shown, have been described above with reference to FIGS. 11A to 11D. The results provided by defect analysis circuits 70A and 70B for the images of the "lack" type and of the "spreading" type defects, respectively, are processed by an OR circuit 95 which provides the accepted/rejected decision elements to computer 30 through bus 42. A delay circuit (adjustable delay t) 96 is also shown on FIG. 12. It allows $I_{EXA}$ to be delayed to cause this image to be processed in phase in compare circuits 70A and 70B with $I_{REF\ max}$ and $I_{REF\ min}$ which have already been submitted to a previous processing step in blocks 47 and 56.

Another Possible Embodiment

Another embodiment of the present invention consists in processsing only the image of the object to be inspected through the above indicated steps, i.e., picking up and sampling (1), thresholding (2), cleaning (3) and centering (4). The image of the reference object has been definitively stored into the computer. The memory of the computer can be provided with a great number of electronic images of various reference objects which can be for instance, modules showing different topologies or lay out corresponding to different part numbers, or masks. In the latter application, the binary data corresponding to the images can be the ones directly provided by the Gerber type patterns generators. The electronic images of the reference object and of the object to be inspected can be centered with respect to marks provided on the objects. This technique is well known for the masks as for the chips in which the alignment problems are of major importance. Then, one obtains electronic images $I_{REF}$ stored in a memory and which can be called by the computer to be processed in the processing unit as indicated above. Bubble memories (or disks) can be used due to the great number of bits to be stored (for instance, 4 megabits), which corresponds to a pixel matrix of 2048×2048 bits, which appears sufficient for sorting masks (10× reticles) and modules.

While the invention has been particularly shown and described with reference to a preferred embodiment thereof, it will be understood by those skilled in the art that numerous changes in form and detail may be made therein without departing from the spirit and scope of the invention.

Having thus described our invention, what we claim as new, and desire to secure by Letters Patent is:

1. A process for inspecting and automatically sorting objects showing patterns provided with constant dimensional tolerances, of the type including the comparison of image $I_{ref}$ of a reference object with image $I_{exa}$ of an object to be inspected, wherein image $I_{exa}$ being able to show geometrical defects with respect to the reference object, said process characterized in that it includes the following steps:

Step 1, processing images $I_{ref}$ and $I_{exa}$ to provide electronic binary images $I_{REF}$ and $I_{EXA}$, respectively, Step 2, defining a structuring element B for each image point of the said electronic binary image and adapted to the dimensional tolerances of the said object to be inspected and the construction of the electronic images $I_{REF\ max}$ and $I_{REF\ min}$ which consist in image $I_{REF}$ expanded and eroded respectively by structuring element B, Step 3, forming the images of the "spreading" or "lack" type defects by respectively carrying out the following logic operations:

$[I_{REF\ max}\ OR\ I_{EXA}]$ EXC. OR $I_{REF\ max}$ and $[I_{REF\ min}\ OR\ I_{EXA}]$ EXC. OR $I_{EXA}$ and Step 4, analyzing the defects with respect to a reject criterion which defines a maximum allowed size for the defects.

2. Inspecting and sorting process as set forth in claim 1 characterized in that the maximum allowed size is determined by the calculation of the horizontal and vertical projections of the defects which define an analysis window.

3. Inspecting and sorting process as set forth in claim 1, characterized in that the step 2 provided for constructing images $I_{REF}$ and $I_{EXA}$ comprises:

picking up images $I_{ref}$ and $I_{exa}$ of the reference object and of the object to be inspected, and thresholding the images to obtain electronic binary images.

4. Inspecting and sorting process as set forth in claim 1, characterized in that the step 2 provided for constructing images $I_{REF}$ and $I_{EXA}$ comprises:

picking up image $I_{exa}$ of the object to be inspected and thresholding this image to obtain an electronic binary image $I_{EXA}$, directly constructing the reference object in binary mode either from a digital pattern generator or from a data bank.

5. Inspecting and sorting process as set forth in claim 3 characterized in that it further includes a step for centering electronic images $I_{REF}$ and $I_{EXA}$, which corresponds to the optical centering of images $I_{ref}$ and $I_{exa}$.

6. Inspecting and sorting process as set forth in claim 3 characterized in that the image picking up step provides analog images including black and white and grey levels.

7. Inspecting and sorting process as set forth in claim 6 characterized in that the picking up step further includes a step for discretizing the image to retain only a number $2^N$ of grey levels, N being between 2 and 6.

8. Inspecting and sorting process as set forth in claim 7 characterized in including an image point intensity frequency curve and wherein the thresholding step includes the threshold determination which is performed from the image point intensity frequency curve, said determination being carried out by using a program.

9. Inspecting and sorting process as set forth in claim 3 characterized in that it further includes a step for cleaning images $I_{REF}$ and $I_{EXA}$ (noise suppression), performed prior to the defect image forming step, and consisting in an erode operation, the size of the structuring element which is to erode the image being smaller than the size of the smallest defect which is to be detected, followed by an expand operation which returns the image to its size prior to said erosion.

10. Apparatus for carrying out the process for inspecting and automatically sorting objects showing patterns with constant dimensional tolerances, of the type including the comparison of image $I_{ref}$ of a reference object with image $I_{exa}$ of an object to be inspected, wherein image $I_{exa}$ being able to show geometrical defects with respect to the reference object, characterized in that it includes:

means for processing images $I_{ref}$ and $I_{exa}$ to provide electronic binary images $I_{REF}$ and $I_{EXA}$, respectively, means for picking up at least image $I_{exa}$ of the object to be inspected, means for constructing binary electronic images $I_{REF}$ and $I_{EXA}$, processing means including means for constructing electronic images $I_{REF\ max}$ and $I_{REF\ min}$, respectively, which are the images of $I_{REF}$ expanded and eroded respectively by a previously determined structuring element B and directly linked to the dimensional tolerances of said patterns, compare means for constructing the images of the "lack" and "spreading" type defects by performing the following logic operations:

$$[I_{REF\ max}\ OR\ I_{EXA}]\ EXCL.\ OR\ I_{REF\ max}\ \text{and}\ [I_{REF\ min}\ OR\ I_{EXA}]\ EXCL.\ OR\ I_{EXA},$$

and means for analyzing defects with repect to predetermined reject criteria and means for sorting and selecting the objects which are accepted.

11. Apparatus as set forth in claim 10 characterized in that pick up means are chosen from the group consisting of the electron microscopes, the TV cameras, the photodiode array and the charge coupled devices.

12. Apparatus as set forth in claim 10 characterized in that said means for constructing binary electronic images $I_{REF}$ and $I_{EXA}$ comprise a threshold detection and thresholding unit.

13. Apparatus as set forth in claim 10, characterized in that it further includes:

compute means for recentering electronic images $I_{REF}$ and $I_{EXA}$.

14. Apparatus as set forth in claim 10 characterized in that said reject criteria are based upon the maximum allowed projections of the defect image on axis x and y, in order to check that a defect can be accepted only if it is really contained within an analysis window the sides of which correspond to said maximum projections.

15. Apparatus as set forth in claim 10 characterized in that it further includes a digital computer which controls all said means.

16. Apparatus or process as set forth in claim 10 characterized in that said objects consist of modules showing a pattern of conducting lines provided on the surface of a ceramic substrate.

* * * * *